US012630535B2

(12) United States Patent
Lawrence et al.

(10) Patent No.: US 12,630,535 B2
(45) Date of Patent: May 19, 2026

(54) INHIBITORS OF ACK1/TNK2 TYROSINE KINASE

(71) Applicant: H. LEE MOFFITT CANCER CENTER AND RESEARCH INSTITUTE, INC., Tampa, FL (US)

(72) Inventors: Nicholas J. Lawrence, Lutz, FL (US); Harshani Rithma Lawrence, Lutz, FL (US); Derek Duckett, Land O Lakes, FL (US); Gary Reuther, Temple Terrace, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 520 days.

(21) Appl. No.: 18/021,308

(22) PCT Filed: Aug. 16, 2021

(86) PCT No.: PCT/US2021/046116
§ 371 (c)(1),
(2) Date: Feb. 14, 2023

(87) PCT Pub. No.: WO2022/036312
PCT Pub. Date: Feb. 17, 2022

(65) Prior Publication Data

US 2023/0295129 A1 Sep. 21, 2023

Related U.S. Application Data

(60) Provisional application No. 63/229,392, filed on Aug. 4, 2021, provisional application No. 63/065,766, filed on Aug. 14, 2020.

(51) Int. Cl.

| | |
|---|---|
| ***C07D 403/12*** | (2006.01) |
| ***A61K 31/506*** | (2006.01) |
| ***A61K 45/06*** | (2006.01) |
| ***A61P 29/00*** | (2006.01) |
| ***C07D 239/48*** | (2006.01) |
| ***C07D 405/12*** | (2006.01) |
| ***C07D 405/14*** | (2006.01) |

(52) U.S. Cl.
CPC ............ *C07D 403/12* (2013.01); *A61K 45/06* (2013.01); *C07D 405/12* (2013.01)

(58) Field of Classification Search
CPC .. C07D 403/12; C07D 405/12; C07D 405/14; C07D 239/48; A61K 45/06; A61K 31/506; A61K 2300/00; A61P 29/00
See application file for complete search history.

(56) References Cited

U.S. PATENT DOCUMENTS

| | | | | |
|---|---|---|---|---|
| 4,559,157 | A | 12/1985 | Smith et al. | |
| 4,608,392 | A | 8/1986 | Jacquet et al. | |
| 4,820,508 | A | 4/1989 | Wortzman | |
| 4,938,949 | A | 7/1990 | Borch et al. | |
| 4,992,478 | A | 2/1991 | Geria | |
| 5,167,649 | A | 12/1992 | Zook | |
| 6,960,648 | B2 | 11/2005 | Bonny | |
| 9,464,091 | B2 | 10/2016 | Gray et al. | |
| 9,850,216 | B2 * | 12/2017 | Mahajan | C07D 405/12 |
| 10,336,734 | B2 * | 7/2019 | Mahajan | C07D 405/12 |
| 2002/0035243 | A1 | 3/2002 | Imfeld et al. | |
| 2002/0120100 | A1 | 8/2002 | Bonny | |
| 2003/0032594 | A1 | 2/2003 | Bonny | |
| 2017/0044111 | A1 | 2/2017 | Gray et al. | |
| 2018/0215738 | A1 | 8/2018 | Mahajan et al. | |
| 2019/0315726 | A1 | 10/2019 | Lee et al. | |

FOREIGN PATENT DOCUMENTS

| | | | |
|---|---|---|---|
| CN | 105017160 | 12/2017 | |
| CN | 105017160 B * | 12/2017 | C07D 239/48 |
| WO | 2010055117 | 5/2010 | |
| WO | 2015021149 | 2/2015 | |
| WO | 2017023899 | 2/2017 | |
| WO | 2017066428 | 4/2017 | |
| WO | 2020051572 | 3/2020 | |
| WO | 2022036310 | 2/2022 | |
| WO | 2022036313 | 2/2022 | |

OTHER PUBLICATIONS

Machine Translation of CN105017160B spec (Year: 2017).*
Mahajan K, et al. ACK1 tyrosine kinase: targeted inhibition to block cancer cell proliferation. Cancer Lett. 2013; 338:185-92.
Mahajan K, et al. Shepherding AKT and androgen receptor by ACK1 tyrosine kinase. *J. Cell. Physiol.* 2010; 224:327-33.
Mahajan K, et al. Activated Cdc42-associated kinase ACK1 promotes prostate cancer progression via androgen receptor tyrosine phosphorylation. *Proc. Natl. Acad. Sci. USA* 2007; 104:8438-43.
Mahajan K, et al. ACK1-mediated androgen receptor phosphorylation modulates radiation resistance in castration-resistant prostate cancer. *J.Biol. Chem.* 2012; 287(26):22112-22.
Aqeilan Ri, et al. WWOX in biological control and tumorigenesis. *J.Cell. Physiol.* 2007; 212:307-10.
Mahajan K, et al. Activated tyrosine kinase ACK1 promotes prostate tumorigenesis: role of ACK1 in polyubiquitination of tumor suppressor Wwox. *Cancer Res.*2005; 65:10514-23.
Franke TF, et al. The protein kinase encoded by the Akt proto-oncogene is a target of the PDGF-activated phosphatidylinositol 3-kinase. *Cell* 1995; 81:727-36.

(Continued)

*Primary Examiner* — Jeffrey S Lundgren
*Assistant Examiner* — Alexander K. Showalter
(74) *Attorney, Agent, or Firm* — Meunier Carlin & Curfman LLC

(57) ABSTRACT

The present disclosure provides anti-cancer compounds and uses thereof, more particularly inhibitors of ACK1 tyrosine kinase and their use in the treatment of cancer.

14 Claims, No Drawings

(56) References Cited

OTHER PUBLICATIONS

Burgering BM, et al .Protein kinase B (c-Akt) in phosphatidylinositol-3-OH kinase signal transduction. *Nature* 1995; 376:599-602.
Manning BD, et al. AKT/PKB signaling: navigating downstream. *Cell* 2007; 129:1261-74.
Mahajan K, et al. ACK1 mediated AKT/PKB tyrosine 176 phosphorylation regulates its activation. *PloS one* 2010; 5:e9646.
DiMauro EF, et al. Discovery of 4-amino-5,6-biaryl-furo[2,3-d]pyrimidines as inhibitors of Lck: development of an expedient and divergent synthetic route and preliminary SAR. *Bioorg. Med. Chem. Lett.* 2007; 17, 2305-9.
Martin MW, et al. Discovery of novel 2,3-diarylfuro[2,3-b]pyridin-4-amines as potent and selective inhibitors of Lck: synthesis, SAR, and pharmacokinetic properties. *Bioorg. Med. Chem. Lett.* 2007; 17:2299-304.
Mahajan K, et al. ACK1 tyrosine kinase activation correlates with pancreatic cancer progression. *Am. J. Pathol.* 2012; 180:1386-93.
Mahajan K, et al. Effect of ACK1 tyrosine kinase inhibitor on ligand-independent androgen receptor activity. *Prostate* 2010; 70:1274-85.
Kopecky DJ, et al. Identification and optimization of N3,N6-diaryl-1Hpyrazolo[3,4-d]pyrimidine-3,6-diamines as a novel class of ACK1 inhibitors. *Bioorg. Med. Chem. Lett.* 2008; 18:6352-6.
Miduturu CV, et al. High-throughput kinase profiling: a more efficient approach toward the discovery of new kinase inhibitors. *Chem. Biol.* 2011; 18:868-79.
Jin M, et al. Discovery of potent, selective and orally bioavailable imidazo[1,5-a]pyrazine derived ACK1 inhibitors. *Bioorg. Med. Chem. Lett.* 2013; 23:979-84.
Golas JM, et al. SKI-606, a 4-anilino-3-quinolinecarbonitrile dual inhibitor of Src and Abl kinases, is a potent antiproliferative agent against chronic myelogenous leukemia cells in culture and causes regression of K562 xenografts in nude mice. *Cancer Res.* 2003; 63:375-81.
Remsing R, et al. Global target profile of the kinase inhibitor bosutinib in primary chronic myeloid leukemia cells. *Leukemia* 2009; 23:477-85.
Tan DS, et al. Bosutinib inhibits migration and invasion via ACK1 in KRAS mutant non-small cell lung cancer. *Mol. Cancer* 2014; 13:13.
Carter TA, et al. Inhibition of drug-resistant mutants of ABL, KIT, and EGF receptor kinases. *Proc. Natl. Acad. Sci. USA* 2005; 102:11011-6.
Liu Y, et al. Dasatinib inhibits site-specific tyrosine phosphorylation of androgen receptor by ACK1 and Src kinases. *Oncogene* 2010; 29:3208-16.
Li J, et al. A chemical and phosphoproteomic characterization of dasatinib action in lung cancer. *Nat. Chem. Biol.* 2010; 6:291-9.
Galkin AV, et al. Identification of NVP-TAE684, a potent, selective, and 20 efficacious inhibitor of NPM-ALK. *Proc. Natl. Acad. Sci. USA* 2007; 104:270-5.
Davis MI, et al. Comprehensive analysis of kinase inhibitor selectivity. *Nat. Biotechnol.* 2011; 29:1046-51.
Metz JT, et al. Navigating the kinome. *Nat. Chem. Biol.*2011; 7:200-2.
Jiao X, et al. Synthesis and optimization of substituted furo[2,3-d]-pyrimidin-4-amines and 7H-pyrrolo[2,3-d]pyrimidin-4-amines as ACK1 inhibitors. *Bioorg. Med. Chem. Lett.* 2012; 22:6212-7.
Bossi RT, et al. Crystal structures of anaplastic lymphoma kinase in complex with ATP competitive inhibitors. *Biochem.* 2010; 49:6813-25.
Bebbington D, et al. The discovery of the potent aurora inhibitor MK-0457 (VX-680). *Bioorg. Med. Chem. Lett.* 2009;19:3586-92.
Moriarty KJ, et al. The synthesis and SAR of 2-amino-pyrrolo[2,3-d]pyrimidines: a new class of Aurora—A kinase inhibitors. *Bioorg. Med. Chem. Lett.* 2006; 16:5778-83.
Tari LW, et al. Structural basis for 5 the inhibition of Aurora A kinase by a novel class of high affinity disubstituted pyrimidine inhibitors. *Bioorg. Med. Chem. Lett.* 2007; 17:688-691.
Lawrence HR, et al. Development of o-chlorophenyl substituted pyrimidines as exceptionally potent aurora kinase inhibitors. *J. Med. Chem.*2012; 55:7392-416.
Martin MP, et al. A novel mechanism by which small molecule inhibitors induce the DFG flip in Aurora A. *ACS Chem. Biol.* 2012; 7:698-706.
Yang H, et al. Dual Aurora A and JAK2 kinase blockade effectively suppresses malignant transformation. *Oncotarget* 2014; 5:2947-61.
Toyoizumi, et al., "Combined therapy with chemotherapeutic agents and herpes simplex virus type 1 ICP34.5 mutant (HSV-1716) in human non-small cell lung cancer," *Human Gene Therapy*, 1999, 10(18):17.
International Search Report and Written Opinion for International Application No. PCT/US2021/046116 dated Feb. 1, 2022, 10 pages.
Tan et al., Development of Selective Covalent Janus Kinase 3 Inhibitors, Journal of Medicinal Chemistry, Aug. 10, 2015, vol. 58, pp. 6589-6606.
International Search Report and Written Opinion for International Application No. PCT/US2021/046112 dated Jan. 31, 2022, 10 pages.
International Search Report and Written Opinion for International Application No. PCT/US2021/046117 dated Nov. 22, 2021, 12 pages.

* cited by examiner

INHIBITORS OF ACK1/TNK2 TYROSINE KINASE

CROSS-REFERENCE TO RELATED APPLICATIONS

This application is a United States National Phase Patent Application of International Patent Application Number PCT/US2021/046116, filed Aug. 16, 2021, which claims the benefit of priority to U.S. Provisional Application No. 63/065,766, filed Aug. 14, 2020, and U.S. Provisional Application No. 63/229,392, filed Aug. 4, 2021, each disclosure of which is incorporated herein by reference in its entirety.

STATEMENT REGARDING FEDERALLY SPONSORED RESEARCH OR DEVELOPMENT

This invention was made with government support under Grant No. CA211447 awarded by the National Institutes of Health. The Government has certain rights in the invention.

TECHNICAL FIELD

This disclosure relates to anti-cancer compounds and uses thereof, and more particularly to inhibitors of ACK1 tyrosine kinase and their use in the treatment of cancer.

BACKGROUND

ACK1, also known as TNK2, is a non-receptor tyrosine kinase that is expressed in diverse cell types. It integrates signals from several important ligand-activated receptor tyrosine kinases (RTKs), for example, EGFR, MerTK, HER2, PDGFR and insulin receptor to initiate intracellular signaling cascades. The ACK1 tyrosine kinase is aberrantly activated, amplified or mutated in many types of human cancers including prostate, breast, pancreatic, ovarian and lung cancers (Mahajan K, et al. ACK1 tyrosine kinase: targeted inhibition to block cancer cell proliferation. *Cancer Lett.* 2013; 338:185-92). Aberrantly activated ACK1 drives cell growth via a number of molecular mechanisms (Mahajan K, et al. Shepherding AKT and androgen receptor by ACK1 tyrosine kinase. *J. Cell. Physiol.* 2010; 224:327-33). Several recent discoveries underscore its tumor promoting functions. For example, ACK1 phosphorylates the androgen receptor, at Tyr267 in its transactivation domain, in an androgen-independent manner to promote castration resistant prostate cancer (CRPC) growth (Mahajan K, et al. Activated Cdc42-associated kinase ACK1 promotes prostate cancer progression via androgen receptor tyrosine phosphorylation. *Proc. Natl. Acad. Sci. USA* 2007; 104:8438-43; Mahajan K, et al. ACK1-mediated androgen receptor phosphorylation modulates radiation resistance in castration-resistant prostate cancer. *J. Biol. Chem.* 2012; 287(26): 22112-22). ACK1 has been shown to promote prostate tumorigenesis by phosphorylating the WW domain-containing oxidoreductase (Wwox) tumor suppressor (Aqeilan R I, et al. WWOX in biological control and tumorigenesis. *J. Cell. Physiol.* 2007; 212:307-10) on Tyr287 leading to its polyubiquitination and subsequent degradation (Mahajan K, et al. Activated tyrosine kinase ACK1 promotes prostate tumorigenesis: role of ACK1 in polyubiquitination of tumor suppressor Wwox. *Cancer Res.* 2005; 65:10514-23). It has also been shown that ACK1 phosphorylates and activates the key signaling kinase AKT, which plays important roles in human physiology and disease (Franke T F, et al. The protein kinase encoded by the Akt proto-oncogene is a target of the PDGF-activated phosphatidylinositol 3-kinase. *Cell* 1995; 81:727-36; Burgering B M, et al. Protein kinase B (c-Akt) in phosphatidylinositol-3-OH kinase signal transduction. *Nature* 1995; 376:599-602; Manning B D, et al. AKT/PKB signaling: navigating downstream. *Cell* 2007; 129:1261-74). When AKT is phosphorylated on Tyr176 by ACK1 it functionally participates in the progression of breast cancer by suppressing pro-apoptotic pathways (Mahajan K, et al. ACK1 mediated AKT/PKB tyrosine 176 phosphorylation regulates its activation. PloS one 2010; 5:e9646). Conversely knockdown of ACK1 expression by siRNA suppressed AKT activation in MCF7 breast cancer cell line and increased expression of pro-apoptotic genes such as Bim and Fas (Id.). ACK1 transgenic mice developed 20 prostatic intraepithelial neoplasia (PINs), indicating that its activation is crucial in tumorigenesis (Id.). Significant evidence in pre-clinical models therefore validates ACK1 as a target for anticancer drugs, and has driven the development of many ACK1 inhibitors. Selected examples of ACK1 inhibitors are as follows:

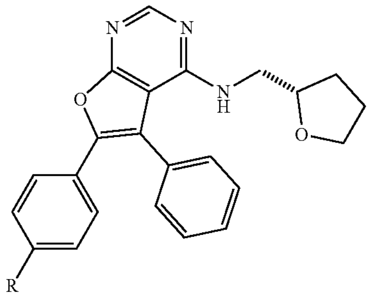

1a R = $O(CH_2)_2NMe_2$
ACK1 $IC_{50}$ 11 nM; Lck $IC_{50}$ 6 nM
1b (AIM-100), R = H
ACK1 $IC_{50}$ 24 nM; Lck $IC_{50}$ 122 nM

1c

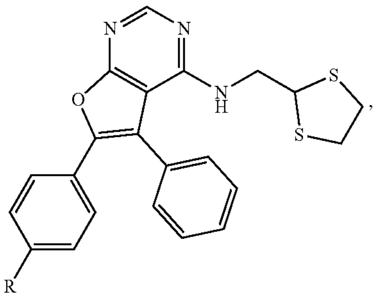

R = $O(CH_2)_2NMe_2$
ACK1 $K_i$ 0.3 nM; Lck $K_i$ 138 nM

-continued

2

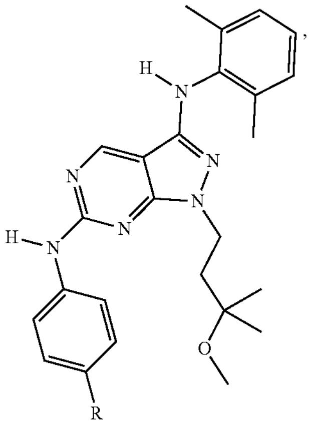

R = H ACK1 $IC_{50}$ 2 nM

-continued

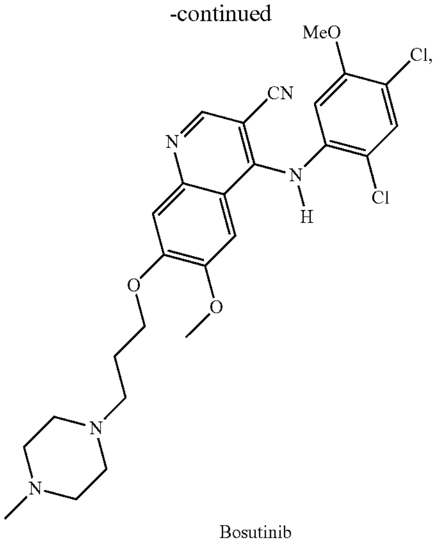

Bosutinib
ACK1 $IC_{50}$ 2.7 nM

3

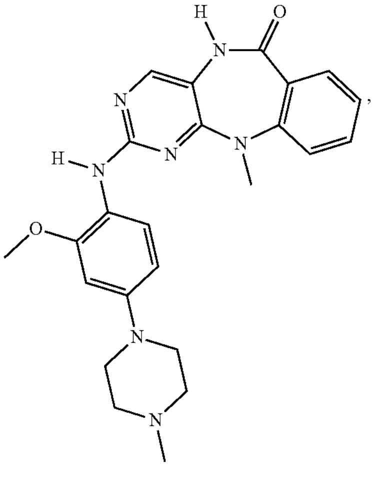

ACK1 $K_d$ 2 nM

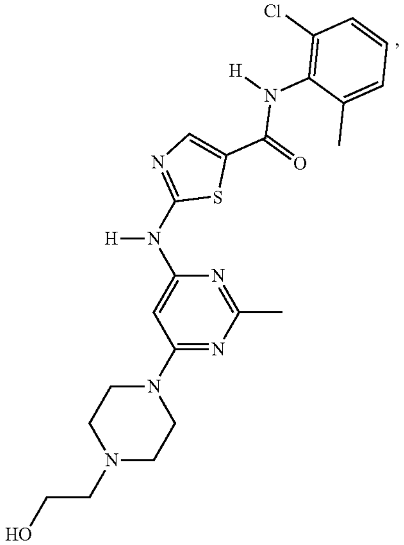

Dasatinib
ACK1 $K_D$ 6 nM

4

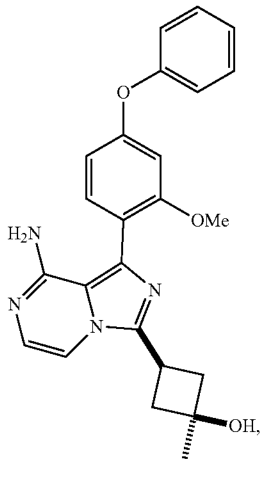

ACK1 $IC_{50}$ 110 nM; ACK1 $IC_{50}$ (cell) 35 nM

A series of 4-amino-5,6-biaryl-furo[2,3-d]pyrimidines (structures 1a-1c) were found to inhibit ACK1 and the related member of the src kinase family Lck (lymphocyte-specific kinase) (DiMauro E F, et al. Discovery of 4-amino-5,6-biaryl-furo[2,3-d]pyrimidines as inhibitors of Lck: development of an expedient and divergent synthetic route and preliminary SAR. *Bioorg. Med. Chem. Lett.* 2007; 17, 2305-9; Martin M W, et al. Discovery of novel 2,3-diaryl-furo[2,3-b]pyridin-4-amines as potent and selective inhibitors of Lck: synthesis, SAR, and pharmacokinetic properties. *Bioorg. Med. Chem. Lett.* 2007; 17:2299-304). For example, compound 1a potently inhibits both ACK1 and Lck and was useful in the development of further compounds for the treatment of T cell-mediated autoimmune and inflammatory disease as a consequence of Lck inhibition. Compound 1b (AIM-100) was used as a chemical probe for ACK1 inhibition, since it was reported to inhibit Lck to a lesser extent (ACK1:Lck 5:1) than 1a (Lck:ACK1 1.8:1). AIM-100 inhibits ACK1 dependent AKT Tyr176 (Mahajan K, et al. ACK1 tyrosine kinase activation correlates with pancreatic cancer progression. *Am. J. Pathol.* 2012; 180: 1386-93) in pancreatic cancer cells and AR Tyr267 (Mahajan K, et al. Effect of ACK1 tyrosine kinase inhibitor on ligand-independent androgen receptor activity. Prostate 2010; 70:1274-85)phosphorylation. AIM-100 also inhibits castration and radioresistant prostate xenograft tumor growth via inhibition of AR Tyr267 phosphorylation (Mahajan K, et al. ACK1-mediated androgen receptor phosphorylation modulates radiation resistance in castration-resistant prostate cancer. *J. Biol. Chem.* 2012; 287:22112-22). A study of further members of the 4-amino-5, 6-biaryl-furo[2,3-d] pyrimidine series showed that the dithiolane 1c was an exceptionally potent ACK1 inhibitor ($K_i$, 0.3 nM). This compound inhibits the growth of a cell line which is dependent upon ACK1 with an $IC_{50}$ of 5 nM. However, its poor pharmacokinetic properties (attributed to oxidation of both the dithiolane ring and $NMe_2$) precluded use in an animal model. A series of pyrazolopyrimidines of type 2 have also been developed by Amgen as ACK1 inhibitors (Kopecky D J, et al. Identification and optimization of N3,N6-diaryl-1H-pyrazolo[3, 4-d]pyrimidine-3,6-diamines as a novel class of ACK1 inhibitors. *Bioorg. Med. Chem. Lett.* 2008; 18:6352-6). For example, compound 2 potently inhibits ACK1 in vitro ($IC_{50}$ 2 nM) and in intact cells, as measured by inhibition of ACK1 autophosphorylation ($IC_{50}$ 20 nM). Gray and co-workers have identified the ACK1 inhibitor 3, by high throughput kinase profiling of a focused library of pyrimidine-diazepines (Miduturu C V, et al. High-throughput kinase profiling: a more efficient approach toward the discovery of new kinase inhibitors. *Chem. Biol.* 2011; 18:868-79). This compound abolishes EGF induced ACK1 autophosphorylation (Tyr284) in HEK293 cells at concentrations of 2 μM. It also inhibits A549 lung cancer cell growth at 10 μM. A series of imidazopyrazine based ACK1 inhibitors have been developed by Jin and co-workers at OSI/Astellas (Jin M, et al. Discovery of potent, selective and orally bioavailable imidazo[1,5-a]pyrazine derived ACK1 inhibitors. *Bioorg. Med. Chem. Lett.* 2013; 23:979-84). For example, compound 4 is a potent ACK1 inhibitor orally bioavailable in mouse models and good experimental ADMET properties. It inhibits ACK1 mediated phosphorylation of poly-(GT) in an AlphaScreen assay with an $IC_{50}$ of 110 nM. It potently inhibits ACK1 in a cellular context. In NCI-H1703 human non-small cell lung cancer cells its $IC_{50}$ for ACK1 inhibition is 35 nM as measured by an ELISA assay. In this assay ACK1 from the cell lysates is captured on an ELISA plate by ACK1 antibodies. The extent of phosphorylation of ACK1 was determined using an enzyme-linked antibody that recognizes phosphotyrosine residues. Several promiscuous kinase inhibitors have been shown to inhibit ACK1. For example, the Src/Abl kinase inhibitor bosutinib (Goias J M, et al. SKI-606, a 4-anilino-3-quinolinecarbonitrile dual inhibitor of Src and Abl kinases, is a potent antiproliferative agent against chronic myelogenous leukemia cells in culture and causes regression of K562 xenografts in nude mice. *Cancer Res.* 2003; 63:375-81) inhibits ACK1 with an $IC_{50}$ of 2.7 nM (Remsing R, et al. Global target profile of the kinase inhibitor bosutinib in primary chronic myeloid leukemia cells. *Leukemia* 2009; 23:477-85). Bosutinib was found to inhibit cell migration and invasion but not viability in a panel of non-small cell lung cancer (NSCLC) cell lines (Tan D S, et al. Bosutinib inhibits migration and invasion via ACK1 in KRAS mutant non-small cell lung cancer. *Mol. Cancer* 2014; 13:13). These effects were not seen when ACK1 was knocked-down specifically in K-Ras mutant cell lines. Dasatinib, another BCR/Abl and Src family tyrosine kinase inhibitor, inhibits ACK1 with a $K_D$ of 6 nM (Carter T A, et al. Inhibition of drug-resistant mutants of ABL, KIT, and EGF receptor kinases. *Proc. Natl. Acad. Sci. USA* 2005; 102:11011-6). Dasatinib was shown to inhibit both ACK1 autophosphorylation and AR phosphorylation of Tyr-267 in heregulin-stimulated human prostate cancer LNCaP cells with $IC_{50}S<5$ nM (Liu Y, et al. Dasatinib inhibits site-specific tyrosine phosphorylation of androgen receptor by ACK1 and Src kinases. *Oncogene* 2010; 29:3208-16). Additionally, dasatinib significantly reduced the growth of LNCaP cells expressing constitutively activated ACK1 in a mouse xenograft model (Id.). Chemical and phosphoproteomic approaches revealed ACK1 to be a target of dasatinib in human lung cancer cells (Li J, et al. A chemical and phosphoproteomic characterization of dasatinib action in lung cancer. *Nat. Chem. Biol.* 2010; 6:291-9). ACK1 inhibitors are developed by analysis of known ACK1 inhibitors including 1b (AIM-100), the pyrazolopyrimidine derivative 5 (Kopecky D J, et al. Identification and optimization of N3,N6-diaryl-1H-pyrazolo[3,4-d]pyrimidine-3,6-diamines as a novel class of ACK1 inhibitors. Bioorg. Med. Chem. Lett. 2008; 18:6352-6) and the ALK inhibitor 6 (TAE684) (Galkin A V, et al. Identification of NVP-TAE684, a potent, selective, and efficacious inhibitor of NPM-ALK. *Proc. Natl. Acad. Sci. USA* 2007; 104:270-5) (which strongly cross-inhibits ACK1 from published inhibitor profiling data sets; $K_d$ 2 nM (Davis M I, et al. Comprehensive analysis of kinase inhibitor selectivity. *Nat. Biotechnol.* 2011; 29:1046-51) and $K_i$ 1 nM (Metz J T, et al. Navigating the kinome. *Nat. Chem. Biol.* 2011; 7:200-2)). The binding modes of the three inhibitors are shown in FIG. 1A through 1F, as derived from the X-ray structure of 5 with ACK1 (pdb 3EQR); 1b (AIM-100) modeled from the X-ray structure of an analog with ACK1 (Jiao X, et al. Synthesis and optimization of substituted furo[2,3-d]-pyrimidin-4-amines and 7H-pyrrolo [2,3-d]pyrimidin-4-amines as ACK1 inhibitors. *Bioorg. Med. Chem. Lett.* 2012; 22:6212-7) (pdb 4EWH); 6 modeled from its X-ray structure with ALK (Bossi R T, et al. Crystal structures of anaplastic lymphoma kinase in complex with ATP competitive inhibitors. *Biochem.* 2010; 49:6813-25) (pdb 2XB7). These bind the ACK1 hinge residues Ala-208 via the pyrimidyl group, positioning groups in the hydrophobic pocket beyond the gatekeeper, and in the ribose binding region (Galkin A V, et al. Identification of NVP-TAE684, a potent, selective, and efficacious inhibitor of NPM-ALK. *Proc. Natl. Acad. Sci. USA* 2007; 104:270-5). The bisanilinopyrimidine scaffold has been long recognized as a classical kinase inhibitor motif (Bebbington D, et al. The discovery of the potent aurora inhibitor MK-0457 (VX-680). *Bioorg. Med. Chem. Lett.* 2009; 19:3586-92; Moriarty K J, et al. The synthesis and SAR of 2-amino-pyrrolo[2,3-d]pyrimidines: a new class of Aurora-A kinase inhibitors. *Bioorg. Med. Chem. Lett.* 2006; 16:5778-83; Tari L W, et al. Structural basis for the inhibition of Aurora A kinase by a novel class of high affinity disubstituted pyrimidine inhibitors. *Bioorg. Med. Chem. Lett.* 2007; 17:688-691). Aurora A inhibitors were reported using a bisanilino-pyrimidine scaffold (Lawrence H R, et al. Development of o-chlorophenyl substituted pyrimidines as exceptionally potent aurora kinase inhibitors. *J. Med. Chem.* 10 2012; 55:7392-416; Martin M P, et al. A novel mechanism by which small molecule inhibitors induce the DFG flip in Aurora A. *ACS Chem. Biol.* 2012; 7:698-706; Yang H, et al. Dual Aurora A and JAK2 kinase blockade effectively suppresses malignant transformation. *Oncotarget* 2014; 5:2947-61). In the development of novel ACK1 inhibitors, the design process incorporated an aminopyrimidine structure as the hinge binding group (FIG. 1D) and the fragments of 1b, 5 and 6 as $R^1$, $R^2$ and $R^3$ (FIG. 1D) groups to create hybrid structures in a mix and match process (FIG. 1A through 1F).

There is a clear need for new compounds and methods for inhibiting ACK1. The present disclosure addresses these needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to anti-cancer compounds their uses thereof. More specifically, the subject matter disclosed herein relates to inhibitors of ACK1 tyrosine kinase and their use in the treatment of cancer.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers “first” and “second” are used solely to aid in distinguishing the various components and steps of the disclosed subject matter. The identifiers “first” and “second” are not intended to imply any particular order, amount, preference, or importance to the components or steps modified by these terms.

As used herein, the term “composition” is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A “pharmaceutically acceptable” component is one that is suitable for use with humans and/or animals without undue adverse side effects (such as toxicity, irritation, and allergic response) commensurate with a reasonable benefit/risk ratio.

“Pharmaceutically acceptable salt” refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

“Pharmaceutically acceptable excipient” refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A “pharmaceutically acceptable carrier” is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, “carrier” includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term “therapeutically effective amount” as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

The present disclosure provides compounds that are ACK1 tyrosine kinase inhibitors. These disclosed compounds can be used in various compositions as anti-cancer therapeutics.

In one aspect, a compound is provided selected from the compounds listed in Table 1:

TABLE 1

ACK1 Inhibitors

| Compound #, Chemical Structure, Name | ACK1 $IC_{50}$ | ACK1 ELISA % Inhibition at 100 nM |
|---|---|---|
| 1 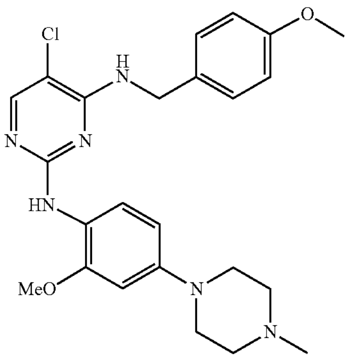 5-chloro-$N^2$-(2-methoxy-4-(4-methylpiperazin-1-yl)phenyl)-$N^4$-(4-methoxybenzyl)pyrimidine-2,4-diamine | 82.9 nM | 70.3 |
| 2 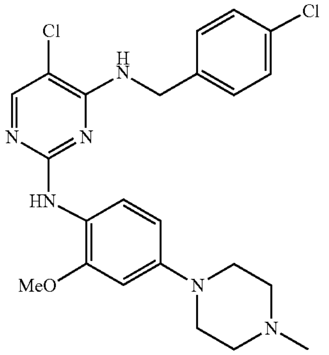 5-chloro-$N^4$-(4-chlorobenzyl)-$N^2$-(2-methoxy-4-(4-methylpiperazin-1-yl)phenyl)pyrimidine-2,4-diamine | | 67.9 |

TABLE 1-continued

ACK1 Inhibitors

| Compound #, Chemical Structure, Name | ACK1 $IC_{50}$ | ACK1 ELISA % Inhibition at 100 nM |
|---|---|---|
| 3 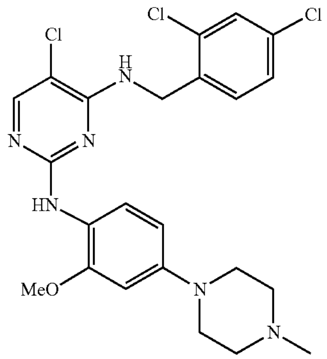 5-chloro-$N^4$-(2,4-dichlorobenzyl)-$N^2$-(2-methoxy-4-(4-methylpiperazin-1-yl)phenyl)pyrimidine-2,4-diamine | 70.1 nM | 78.1 |
| 4 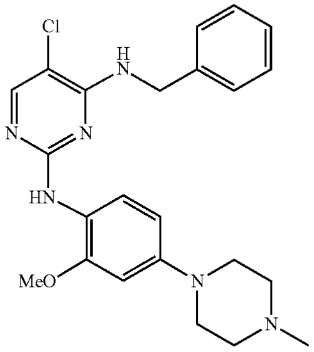 $N^4$-benzyl-5-chloro-$N^2$-(2-methoxy-4-(4-methylpiperazin-1-yl)phenyl)pyrimidine-2,4-diamine | 48.2 nM | 98.2 |
| 5 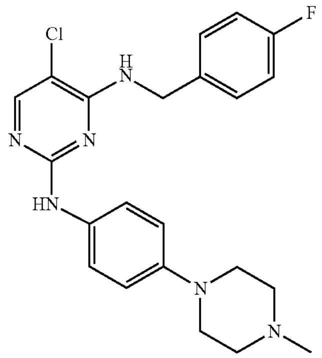 5-chloro-$N^4$-(4-fluorobenzyl)-$N^2$-(4-(4-methylpiperazin-1-yl)phenyl)pyrimidine-2,4-diamine | 35.6 nM | 94.0 |

TABLE 1-continued

ACK1 Inhibitors

| Compound #, Chemical Structure, Name | ACK1 $IC_{50}$ | ACK1 ELISA % Inhibition at 100 nM |
|---|---|---|
| 6<br>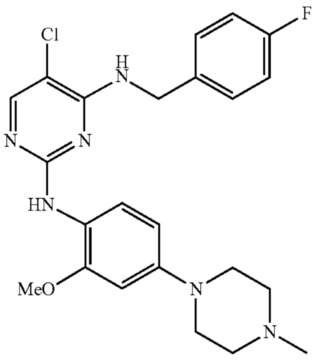<br>5-chloro-$N^4$-(4-fluorobenzyl)-$N^2$-(2-methoxy-4-(4-methylpiperazin-1-yl)phenyl)pyrimidine-2,4-diamine | 43.9 nM | 91.2 |
| 7<br>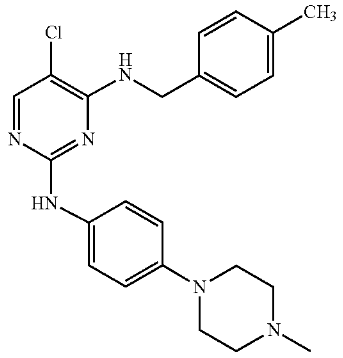<br>5-chloro-$N^4$-(4-methylphenyl)-$N^2$-(4-(4-methylpiperazin-1-yl)phenyl)pyrimidine-2,4-diamine | 42.1 nM | |
| 8<br>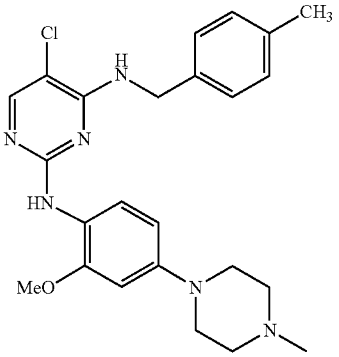<br>5-chloro-$N^2$-(2-methoxy-4-(4-methylpiperazin-1-yl)phenyl)-$N^4$-(4-methylbenzyl)pyrimidine-2,4-diamine | 50.8 nM | 77.6 |
| 9<br>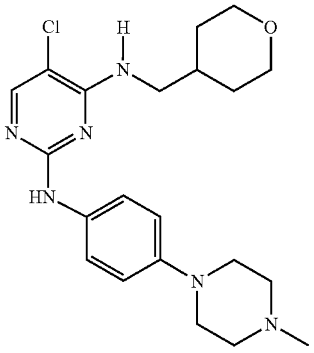<br>5-chloro-$N^2$-(4-(4-methylpiperazin-1-yl)phenyl)-$N^4$-((tetrahydro-2H-pyran-4-yl)methyl)pyrimidine-2,4-diamine | 20.5 nM | |
| 10<br>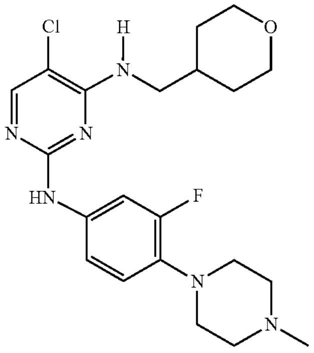<br>5-chloro-$N^2$-(3-fluoro-4-(4-methylpiperazin-1-yl)phenyl)-$N^4$-((tetrahydro-2H-pyran-4-yl)methyl)pyrimidine-2,4-diamine | 19.8 nM | |
| 11<br>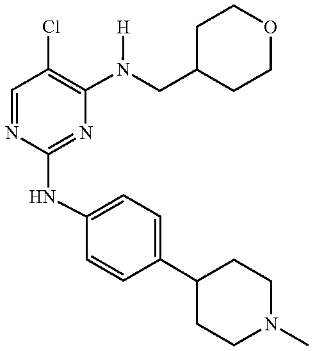<br>5-chloro-$N^2$-(4-(1-methylpiperidin-4-yl)phenyl)-$N^4$-((tetrahydro-2H-pyran-4-yl)methyl)pyrimidine-2,4-diamine | 39.5 nM | |

TABLE 1-continued

| ACK1 Inhibitors | | |
|---|---|---|
| Compound #, Chemical Structure, Name | ACK1 $IC_{50}$ | ACK1 ELISA % Inhibition at 100 nM |
| 12 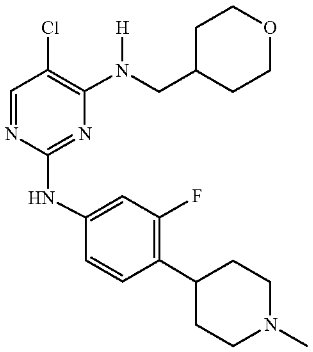 5-chloro-$N^2$-(3-fluoro-4-(1-methylpiperidin-4-yl)phenyl)-$N^4$-((tetrahydro-2H-pyran-4-yl)methyl)pyrimidine-2,4-diamine | 35.9 | |
| 13 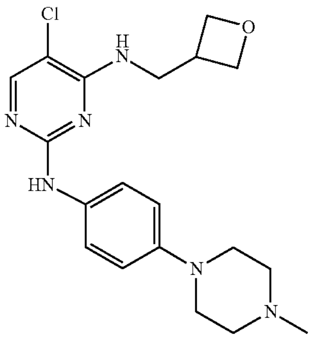 5-chloro-$N^2$-(4-(4-methylpiperazin-1-yl)phenyl)-$N^4$-(oxetan-3-ylmethyl)pyrimidine-2,4-diamine | | |
| 14 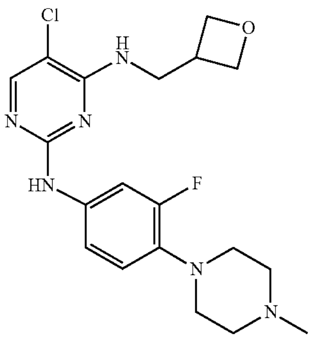 5-chloro-$N^2$-(3-fluoro-4-(4-methylpiperazin-1-yl)phenyl)-$N^4$-(oxetan-3-ylmethyl)pyrimidine-2,4-diamine | | |

TABLE 1-continued

| ACK1 Inhibitors | | |
|---|---|---|
| Compound #, Chemical Structure, Name | ACK1 $IC_{50}$ | ACK1 ELISA % Inhibition at 100 nM |
| 15 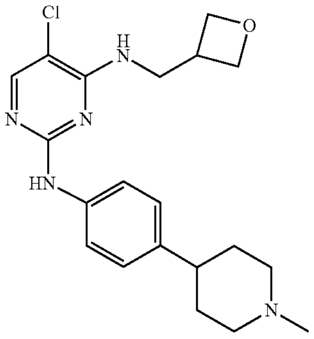 5-chloro-$N^2$-(4-(1-methylpiperidin-4-yl)phenyl)-$N^4$-(oxetan-3-yl)methyl)pyrimidine-2,4-diamine | | |
| 16 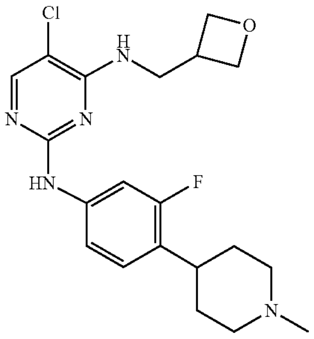 5-chloro-$N^2$-(3-fluoro-4-(1-methylpiperidin-4-yl)phenyl)-$N^4$-(oxetan-3-ylmethyl)pyrimidine-2,4-diamine | | |
| 17 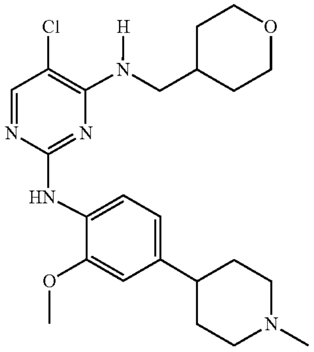 5-chloro-$N^2$-(2-methoxy-4-(1-methylpiperidin-4-yl)phenyl)-$N^4$-((tetrahydro-2H-pyran-4-yl)methyl)pyrimidine-2,4-diamine | 20.2 nM | |

TABLE 1-continued

ACK1 Inhibitors

| Compound #,<br>Chemical Structure,<br>Name | ACK1 $IC_{50}$ | ACK1 ELISA % Inhibition at 100 nM |
|---|---|---|
| 18<br>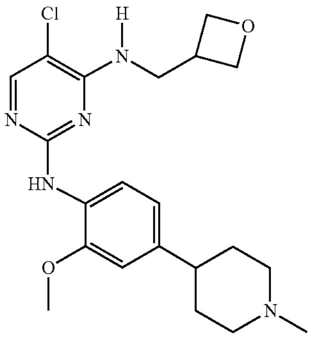<br>5-chloro-$N^2$-(2-methoxy-4-(1-methylpiperidin-4-yl)phenyl)-$N^4$-(oxetan-3-ylmethyl)pyrimidine-2,4-diamine | | |
| 19<br>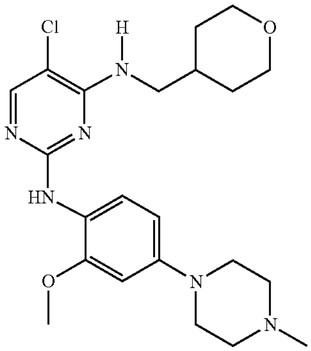<br>5-chloro-$N^2$-(2-methoxy-4-(4-methylpiperazin-1-yl)phenyl)-$N^4$-((tetrahydro-2H-pyran-4-yl)methyl)pyrimidine-2,4-diamine | 14.9 nM | |
| 20<br>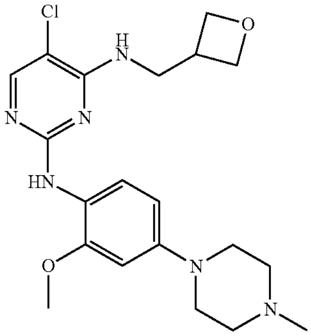<br>5-chloro-$N^2$-(2-methoxy-4-(4-methylpiperazin-1-yl)phenyl)-$N^4$-(oxetan-3-ylmethyl)pyrimidine-2,4-diamine | | |
| 21<br>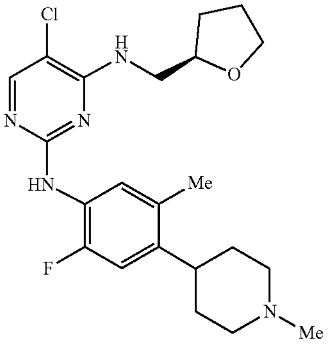<br>(R)-5-chloro-$N^2$-(2-fluoro-5-methyl-4-(1-methylpiperidin-4-yl)phenyl)-$N^4$-((tetrahydrofuran-2-yl)methyl)pyrimidine-2,4-diamine | 85.3 nM | |
| 22<br>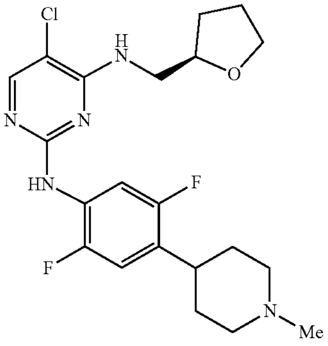<br>(R)-5-chloro-$N^2$-(2,5-difluoro-4-(1-methylpiperidin-4-yl)phenyl)-$N^4$-((tetrahydrofuran-2-yl)methyl)pyrimidine-2,4-diamine | 44.7 nM | |
| 23<br>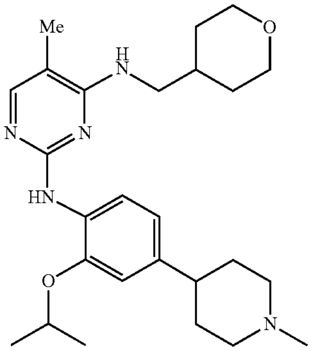<br>$N^2$-(2-isopropoxy-4-(1-methylpiperidin-4-yl)phenyl)-5-methyl-$N^4$-((tetrahydro-2H-pyran-4-yl)methyl)pyrimidine-2,4-diamine | | |

TABLE 1-continued

| ACK1 Inhibitors | | |
|---|---|---|
| Compound #, Chemical Structure, Name | ACK1 $IC_{50}$ | ACK1 ELISA % Inhibition at 100 nM |
| 24 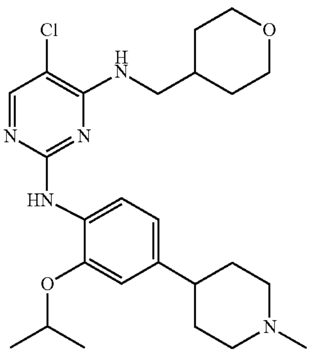 5-chloro-$N^2$-(2-isopropoxy-4-(1-methylpiperidin-4-yl)phenyl)-$N^4$-((tetrahydro-2H-pyran-4-yl)methyl)pyrimidine-2,4-diamine | | |
| 25 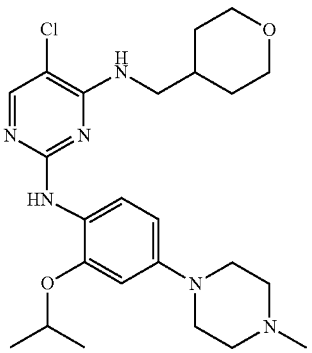 5-chloro-$N^2$-(2-isopropoxy-4-(4-methylpiperazin-1-yl)phenyl)-$N^4$-((tetrahydro-2H-pyran-4-yl)methyl)pyrimidine-2,4-diamine | | |

TABLE 1-continued

| ACK1 Inhibitors | | |
|---|---|---|
| Compound #, Chemical Structure, Name | ACK1 $IC_{50}$ | ACK1 ELISA % Inhibition at 100 nM |
| 26 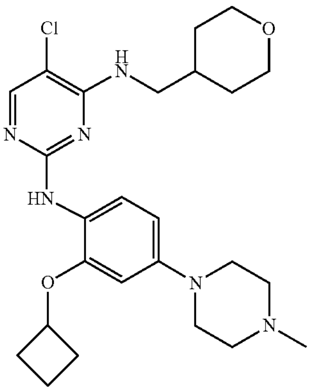 5-chloro-$N^2$-(2-cyclobutoxy-4-(1-methylpiperidin-4-yl)phenyl)-$N^4$-((tetrahydro-2H-pyran-4-yl)methyl)pyrimidine-2,4-diamine | | |

In an alternative aspect, a compound is provided selected from the compounds listed in Table 2:

TABLE 2

| Further ACK1 Inhibitors | |
|---|---|
| Compound #, Chemical Structure, Name | ACK1 $IC_{50}$ (nM) (Reaction Biology $^{33}P$ Hotspot assay) |
| 27 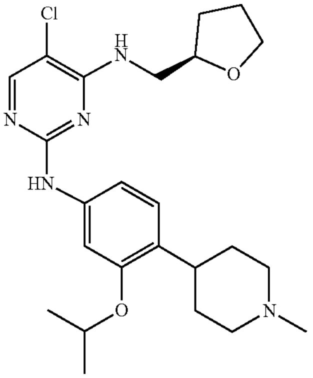 (R)-5-chloro-$N^2$-(3-isopropoxy-4-(1-methylpiperidin-4-yl)phenyl)-$N^4$-((tetrahydrofuran-2-yl)methyl)pyrimidine-2,4-diamine | 62.0 |

TABLE 2-continued

| Further ACK1 Inhibitors | |
|---|---|
| Compound #, Chemical Structure, Name | ACK1 $IC_{50}$ (nM) (Reaction Biology $^{33}P$ Hotspot assay) |
| 28 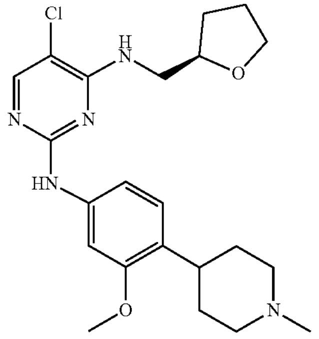 (R)-5-chloro-$N^2$-(3-methoxy-4-(1-methylpiperidin-4-yl)phenyl)-$N^4$-((tetrahydrofuran-2-yl)methyl)pyrimidine-2,4-diamine | 87.2 |
| 29 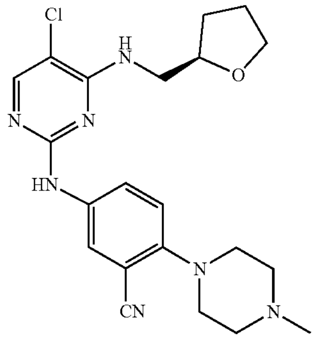 (R)-5-((5-chloro-4-(((tetrahydrofuran-2-yl)methyl)amino)pyrimidin-2-yl)amino-2-(4-methylpiperazin-1-yl)benzonitrile | 112 |
| 30 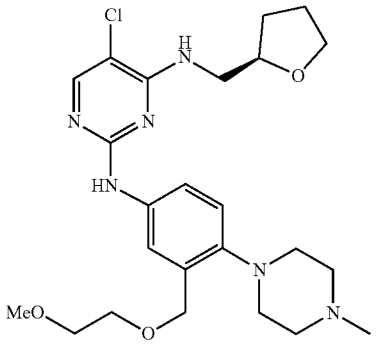 (R)-5-chloro-$N^2$-(3-((2-methoxyethoxy)methyl)-4-(4-methylpiperazin-1-yl)phenyl)-$N^4$-((tetrahydrofuran-2-yl)methyl)pyrimidine-2,4-diamine | 198 |

TABLE 2-continued

| Further ACK1 Inhibitors | |
|---|---|
| Compound #, Chemical Structure, Name | ACK1 $IC_{50}$ (nM) (Reaction Biology $^{33}P$ Hotspot assay) |
| 31 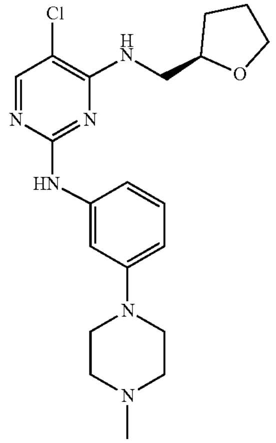 (R)-5-chloro-$N^2$-(3-(4-methylpiperazin-1-yl)phenyl)-$N^4$-((tetrahydrofuran-2-yl)methyl)pyrimidine-2,4-diamine | 88 |
| 32 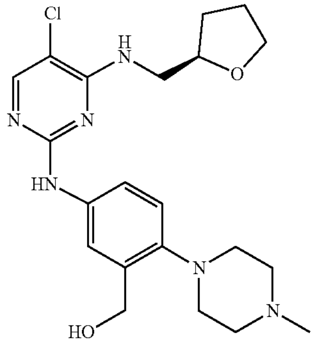 (R)-5-((5-chloro-4-(((tetrahydrofuran-2-yl)methyl)amino)pyrimidin-2-yl)amino)-2-(4-methylpiperazin-1-yl)phenyl)methanol | 51 |

TABLE 2-continued

Further ACK1 Inhibitors

| Compound #, Chemical Structure, Name | ACK1 $IC_{50}$ (nM) (Reaction Biology $^{33}P$ Hotspot assay) |
|---|---|
| 33<br>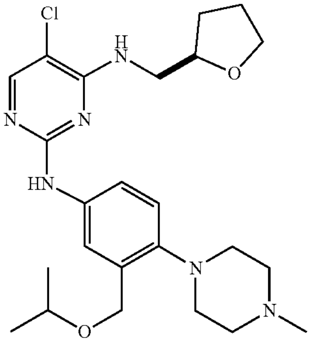<br>(R)-5-chloro-$N^2$-(3-(isopropoxymethyl)-4-(4-methylpiperazin-1-yl)phenyl)-$N^4$-((tetrahydrofuran-2-yl)methyl)pyrimidine-2,4-diamine | 167 |
| 34<br>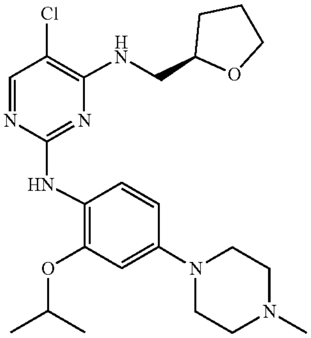<br>(R)-5-chloro-$N^2$-(2-isopropoxy-4-(4-methylpiperazin-1-yl)phenyl)-$N^4$-((tetrahydrofuran-2-yl)methyl)pyrimidine-2,4-diamine | |
| 35<br>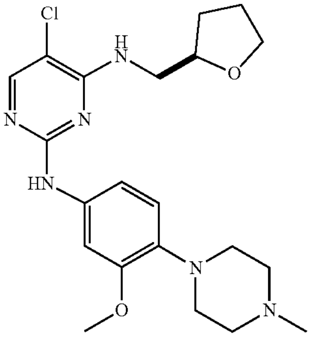<br>(R)-5-chloro-$N^2$-(3-methoxy-4-(4-methylpiperazin-1-yl)phenyl)-$N^4$-((tetrahydrofuran-2-yl)methyl)pyrimidine-2,4-diamine | |

TABLE 2-continued

Further ACK1 Inhibitors

| Compound #, Chemical Structure, Name | ACK1 $IC_{50}$ (nM) (Reaction Biology $^{33}P$ Hotspot assay) |
|---|---|
| 36<br>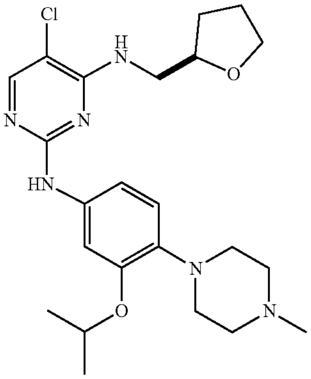<br>(R)-5-chloro-$N^2$-(3-isopropoxy-4-(4-methylpiperazin-1-yl)phenyl)-$N^4$-((tetrahydrofuran-2-yl)methyl)pyrimidine-2,4-diamine | |
| 37<br>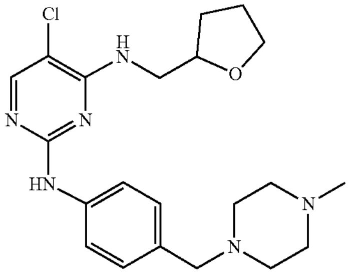<br>5-chloro-$N^2$-(4-((4-methylpiperazin-1-yl)methyl)phenyl)-$N^4$-((tetrahydrofuran-2-yl)methyl)pyrimidine-2,4-diamine | 145 |
| 38<br>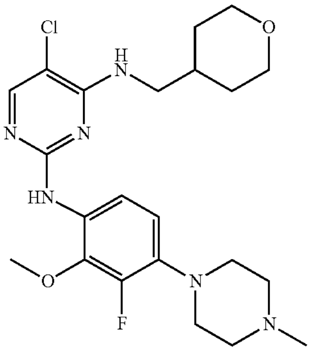<br>5-chloro-$N^2$-(3-fluoro-2-methoxy-4-(4-methylpiperazin-1-yl)phenyl)-$N^4$-((tetrahydro-2H-pyran-4-yl)methyl)pyrimidine-2,4-diamine | 87.9 |

TABLE 2-continued

| Further ACK1 Inhibitors | |
|---|---|
| Compound #, Chemical Structure, Name | ACK1 $IC_{50}$ (nM) (Reaction Biology $^{33}P$ Hotspot assay) |
| 39 | 11.9 |
| 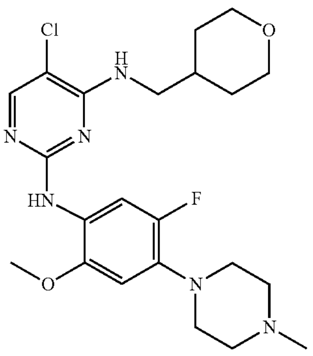 | |
| 5-chloro-$N^2$-(5-fluoro-2-methoxy-4-(4-methylpiperazin-1-yl)phenyl)-$N_4$-((tetrahydro-2H-pyran-4-yl)methyl)pyrimidine-2,4-diamine | |
| 40 | 26.6 |
| 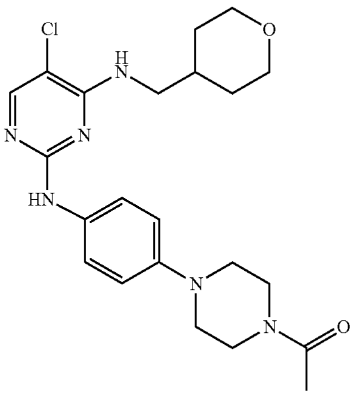 | |
| 1-(4-(4-((5-chloro-4-(((tetrahydro-2H-pyran-4-yl)methyl)amino)pyrimidin-2-yl)amino)phenyl)piperazin-1-yl)ethan-1-one | |
| 41 | 17.3 |
| 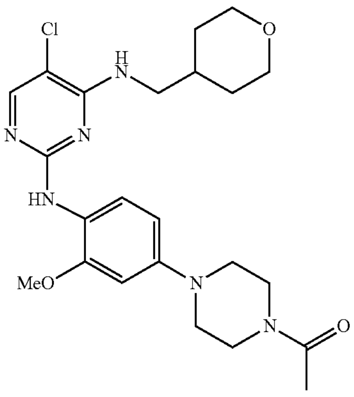 | |

TABLE 2-continued

| Further ACK1 Inhibitors | |
|---|---|
| Compound #, Chemical Structure, Name | ACK1 $IC_{50}$ (nM) (Reaction Biology $^{33}P$ Hotspot assay) |
| 1-(4-(4-((5-chloro-4-(((tetrahydro-2H-pyran-4-yl)methyl)amino)pyrimidin-2-yl)amino)-3-methoxyphenyl)piperazin-1-yl)ethan-1-one | |
| 42 | 9.87 |
| 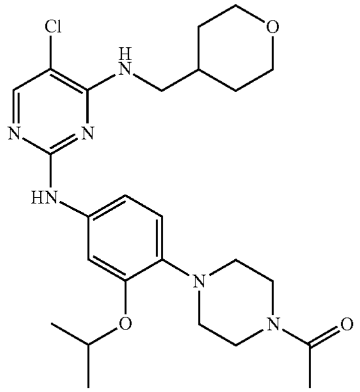 | |
| 1-(4-(4-((5-chloro-4-(((tetrahydro-2H-pyran-4-yl)methyl)amino)pyrimidin-2-yl)amino)-2-isopropoxyphenyl)piperazin-1-yl)ethan-1-one | |

The disclosed compounds can also exist as pharmaceutically acceptable salts and examples of such salts are disclosed herein.

Methods of Use

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

A cancer immunotherapeutic agent suitable for use in the methods disclosed herein is an immunotherapeutic agent which comprises a cell effector component joined to a tumor associated antigen targeting component. Suitable cell effector components can include cytotoxic chemicals, cytotoxic radioisotopes, and cell signaling agents such as cytokines. Suitable tumor targeting components are polypeptide chains which bind to tumor associated antigens present on or in the surrounding tissue matrix of a tumor cell such as receptor protein chains or immunoglobulin chains.

Tumor associated antigens which can be used for targets of the immunotherapeutic agents include a tumor associated antigen selected from the group consisting of AFP, CA 125, CEA, CD19, CD20, CD44, CD45, EGF Receptor, GD[2], GD[3], GM1, GM2, Her-2/Neu, Ep-CAM (KSA), IL-2 receptor, Lewis-Y, Lewis-X (CD 15), melanoma-associated proteoglycan MCSP, PSA and Transferrin Receptor.

Examples of immunotherapeutic agents have an effector component that is a cytokine polypeptide joined to a targeting component which is an immunoglobulin (Ig) polypeptide chain. The Ig polypeptide chain comprises a variable region which binds to a tumor associated antigen. It is preferred that said immunoglobulin chain, when combined with the appropriate complementary chain (i.e. a heavy chain complements a light chain) defines an antibody active site which is specific for a tumor associated antigen.

The tumor targeting Ig portion of the immunotherapeutic agent can comprise an entire immunoglobulin chain amino acid sequence, or at least the fragment of which comprises the antigen binding specificity portion of the protein. Thus, a suitable Ig polypeptide chain will have at least an Ig variable region specific for a tumor associated antigen.

An antibody and polypeptide chains therefrom, suitable for use in the disclosed methods, will have an amino acid sequence that can be of any mammalian origin. Where such antibody protein is not of the same origin as the anticipated patient, fragments of the antibody protein, such as F(ab')2, Fab, Fv or engineered Fv single chain antibody protein can be used. To further reduce antigenicity of the antibody protein, modification of the antibody amino acid sequence may be accomplished to reduce such by making the protein appear more like the patient's normal antibody components. For example, monoclonal murine antibody amino acid sequences can be modified to appear more human, for administration to human patients by a variety of processes for humanization of the antibody.

Specific examples of cancer immunotherapeutic agents include an antibody that specifically binds CLTA-4, such as ipilimumab (Bristol-Myers Squibb), anti-PD-1, anti-PDLE Other immunotherapeutic agents include the TNFα antagonists (e.g. etanercept), the B cell depleting agent rituximab, the anti-IL-6 receptor tocilizumab, and the costimulation blocker abatacept can be administered with the compounds or compositions disclosed herein.

The disclosed compounds can also be administered with toll like receptor (TLR) agonist. TLR agonist is a ligand for a TLR selected from the group consisting of TLR1, TLR2, TLR3, TLR4, and TLR9. For example, the TLR agonist can be a ligand selected from the group consisting of Pam3CSK4, Pam3CSK4, poly I:C, Ribomunyl, and CpG ODN.

The disclosed compounds can also be administered with an angiogenesis inhibiting agent, which is one which can inhibit the formation of new blood vessels (neovascularization) or enlargement of existing capillary networks into the tissues near a tumor cell. Suitable angiogenesis inhibiting agents can be peptides with angiogenesis inhibiting activity, such as the tumor associated antigen PSA. Other suitable angiogenesis inhibiting agents can be antagonists of VEGF associated angiogenesis, for example antagonists of the VEGF receptor on the surface of cells. One monoclonal antibody which can be used is LM609 (ATCC HB 9537).

Methods of Administration

The disclosed compounds can be administered either sequentially or simultaneously in separate or combined pharmaceutical formulations. When one or more of the disclosed compounds is used in combination with a second therapeutic agent, the dose of each compound can be either the same as or differ from that when the compound is used alone. Appropriate doses will be readily appreciated by those skilled in the art.

The term "administration" and variants thereof (e.g., "administering" a compound) in reference to a compound as described herein means introducing the compound or a prodrug of the compound into the system of the animal in need of treatment. When a compound as described herein or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 2003/0032594 and 2002/0120100 disclose amino acid sequences that can be coupled to another composition and that allows the composition to be translocated across biological membranes. U.S. Application Publication No. 2002/0035243 also describes compositions for transporting biological moieties across cell membranes for intracellular delivery. Compounds can also be incorporated into polymers, examples of which include poly(D-L lactide-co-glycolide) polymer for intracranial tumors; poly[bis(p-carboxyphenoxy) propane: sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," Human Gene Therapy, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation; East Hanover, NJ) and HERCEPTIN (Genentech, Inc.; South San Francisco, CA), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$ etc.), and toxins of bacterial, fungal, plant, or animal origin (e.g., ricin, botulinum toxin, anthrax toxin, aflatoxin, jellyfish venoms (e.g., box jellyfish, etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods described herein are further provided. By "kit" is intended any manufacture (e.g., a package or a container) comprising at least one reagent, e.g., anyone of the compounds described in Table 1. The kit can be promoted, distributed, or sold as a unit for performing the methods described herein. Additionally, the kits can contain a package insert describing the kit and methods for its use. Any or all of the kit reagents can be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Compound Synthesis

The compounds disclosed herein can be prepared by the following general route:

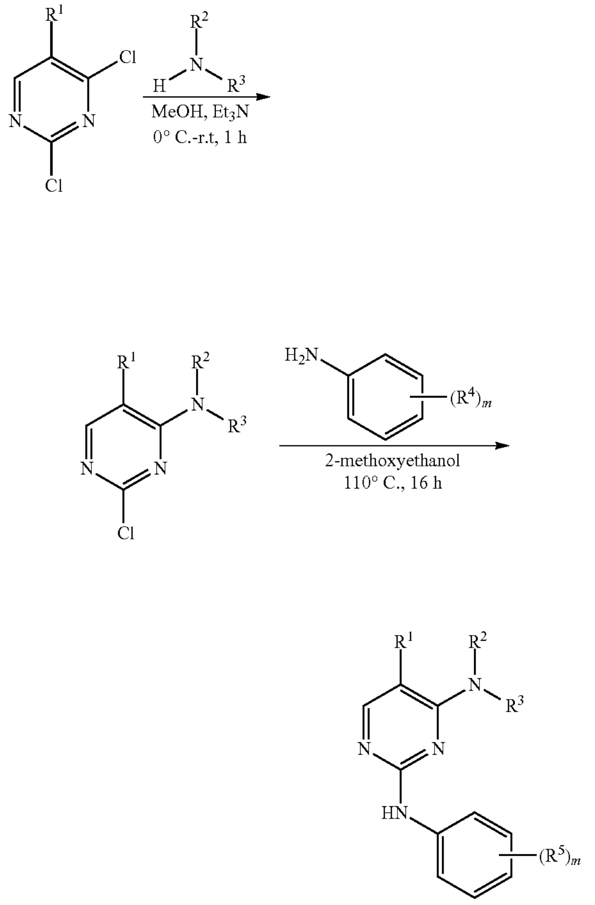

For example, the compounds can be prepared by a route disclosed in WO2015/021149 and WO 2017/023899, each of which is incorporated by reference herein for its synthetic techniques and characterization assays.

Representative syntheses of intermediates as may be used in the first step of the above route are provided below:

Intermediate 1

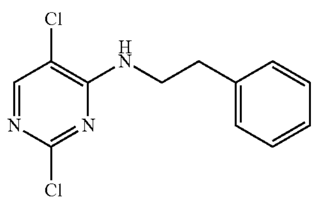 [SMILES: Clc1ncc(Cl)c(NCCc2ccccc2)n1]

2,5-Dichloro-N-phenethylpyrimidin-4-amine (Int-1): To a solution of phenylethylamine (0.628 g, 5.180 mmol) in MeOH (10 mL) under Argon at 0° C. was added $Et_3N$ (0.76 mL, 5.453 mmol). The reaction mixture was stirred at 0° C. for 10 min., followed by adding solution of 2,4,5-trichloropyrimidine (1.000 g, 5.453 mmol) in MeOH slowly. The reaction mixture was warmed up to r.t. after addition and stirred for 2 h. The solvent was removed and the resulting residue was diluted with EtOAc (50 mL) and washed with water (25 mL), then brine (20 mL). The organic layer was dried ($Na_2SO_4$), filtered and concentrated to obtain the title compound as an orange liquid (1.290 g, 92.8%). $^1$H NMR (400 MHz, $CDCl_3$): δ 7.98 (s, 1H), 7.35-7.21 (m, 5H), 5.57 (brs, 1H), 3.80-3.75 (m, 2H), 2.95-2.92 (t, J=6.8 Hz, 2H).

Intermediate 2

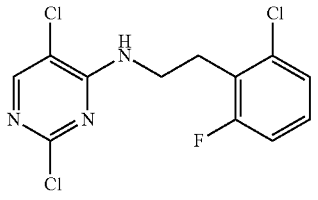 [SMILES: Fc1cccc(Cl)c1CCNc1nc(Cl)ncc1Cl]

2,5-Dichloro-N-(2-chloro-6-fluorophenethyl)pyrimidin-4-amine (Int-2): This was prepared in the same way as Int-1 using 2-fluoro-6-chlorophenylethylamine (0.984 g, 5.180 mmol) to provide the title compound as a white powder (0.972 g, 59%). $^1$H NMR (400 MHz, CD3OD): δ 7.98 (s, 1H), 7.20-7.18 (m, 2H), 7.03-6.99 (m, 1H), 3.775 (t, J=6.8 HZ, 2H), 3.14 (dt, J=2.0 Hz, 6.4 Hz, 2H).

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:
1. A compound selected from:
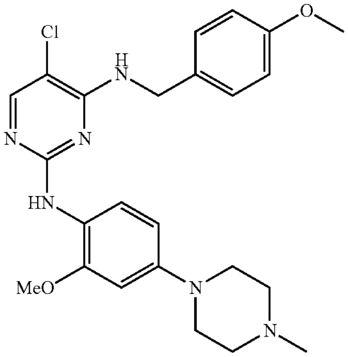
,
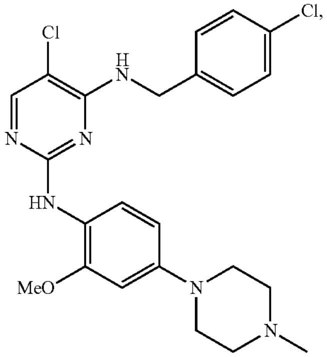
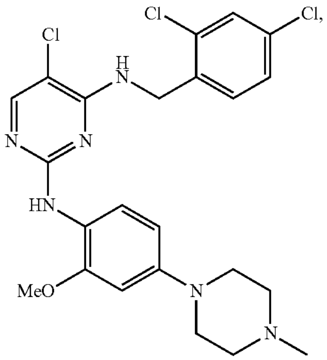
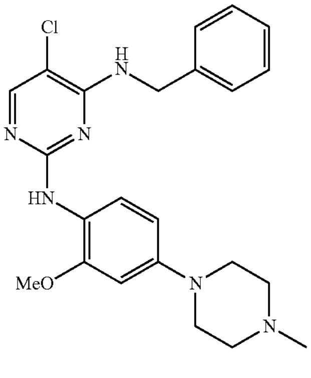
,
-continued
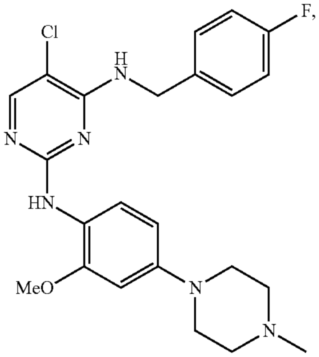
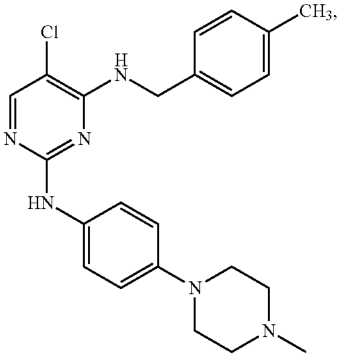
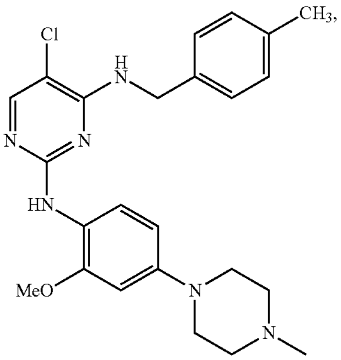
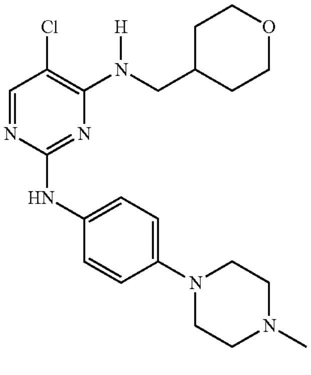
,

-continued
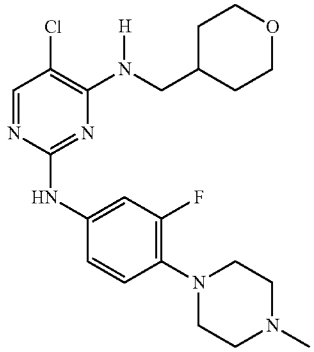
,
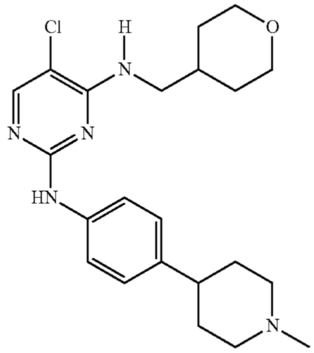
,
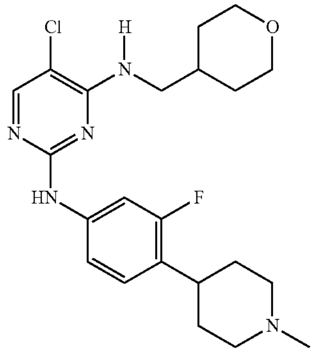
,
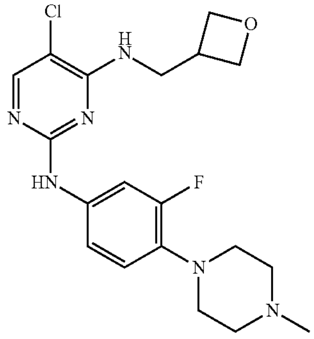
,
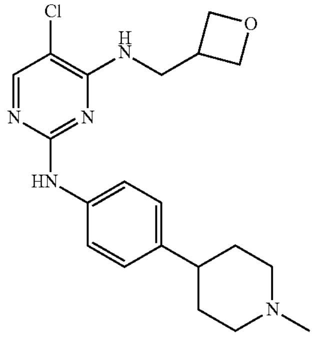
,
-continued
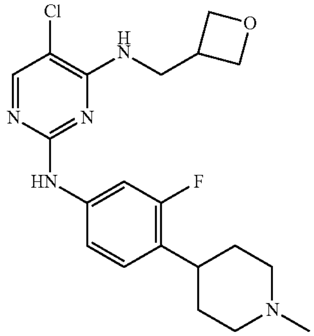
,
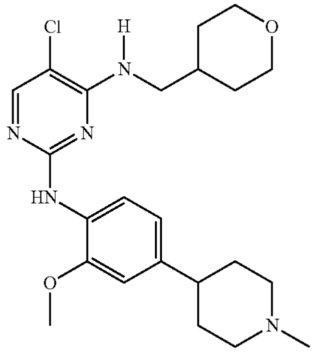
,
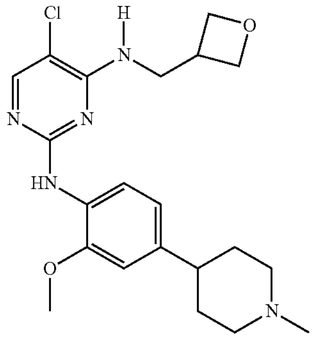
,
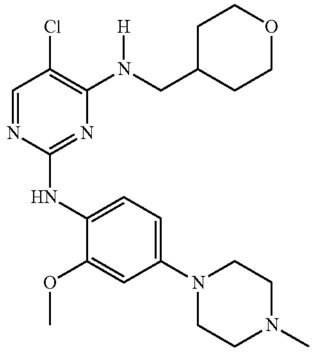
,
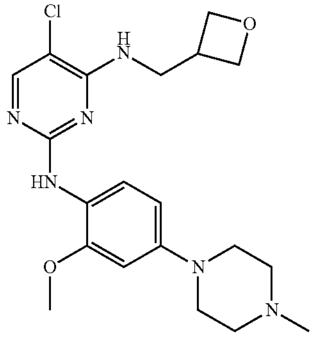
, -continued
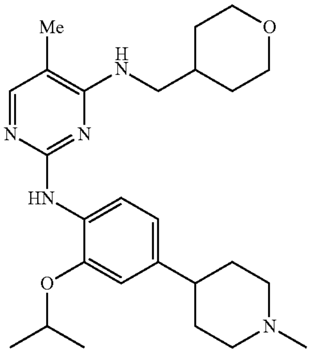
,
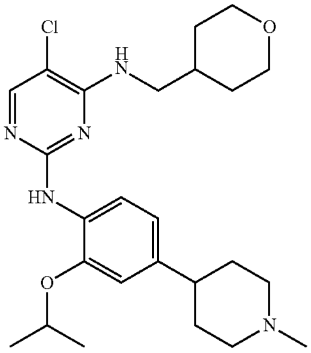
,
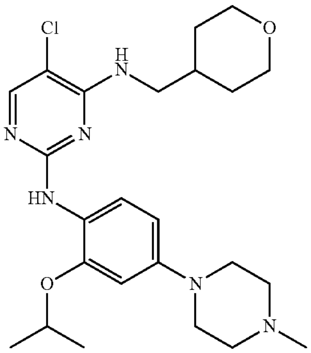
, and
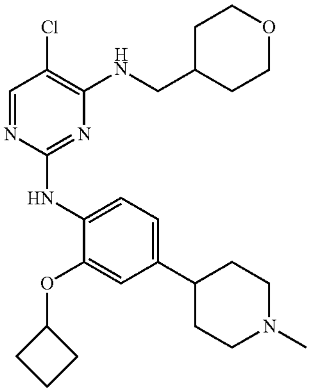
;
or a pharmaceutically acceptable salt thereof.
2. A compound selected from:
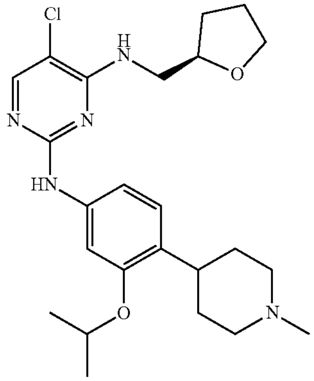
,
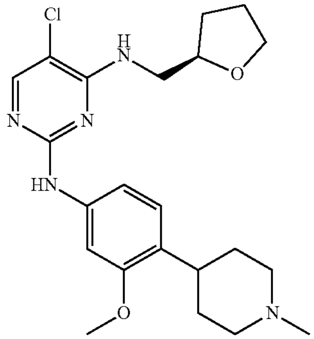
,
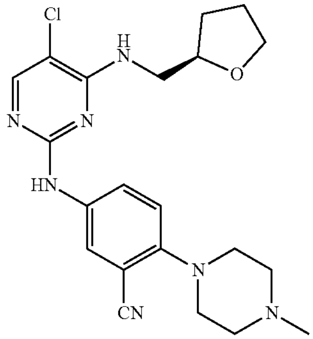
,
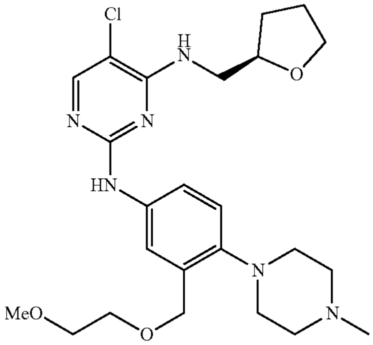
, -continued

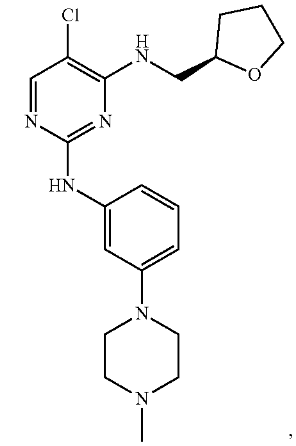

,

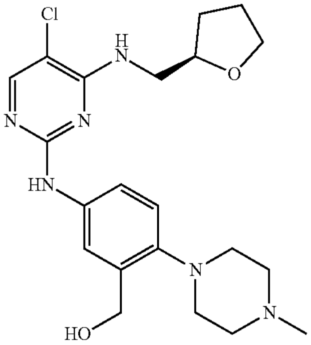

,

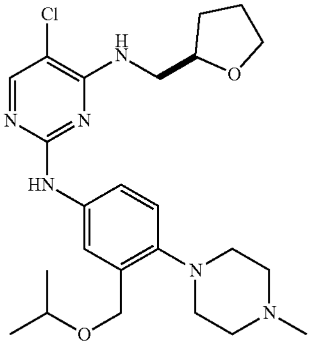

,

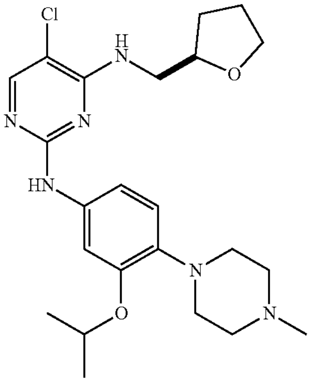

,

-continued

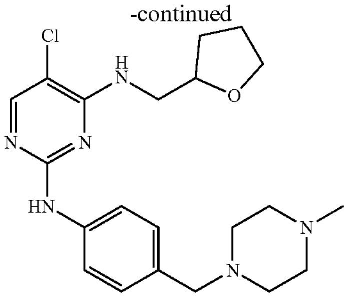

,

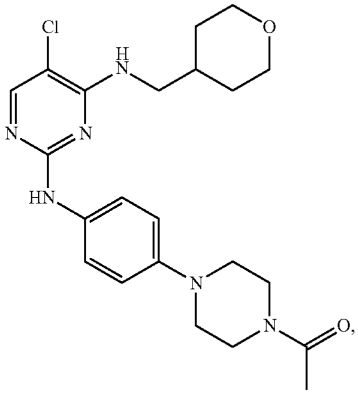

,

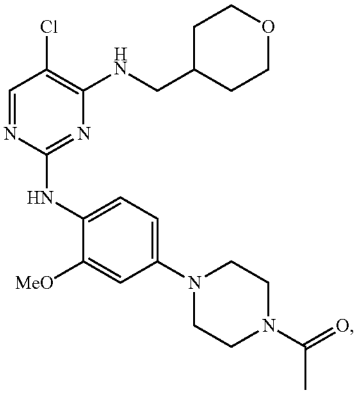

, and

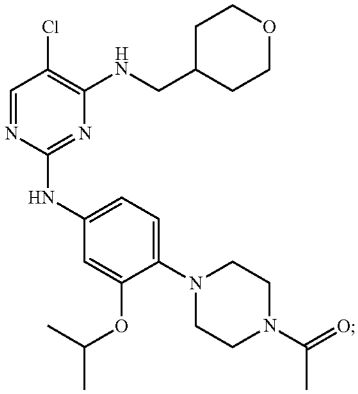

;

or a pharmaceutically acceptable salt thereof.

3. A pharmaceutical composition comprising a compound of claim 1, or a pharmaceutically acceptable salt thereof, and a pharmaceutically acceptable carrier.

4. A method of treating a cancer in a subject in need thereof comprising administering to the subject a therapeutically effective amount of a compound of claim 1, or a pharmaceutically acceptable salt thereof.

5. The method of claim 4, further comprising administering an additional therapeutic agent.

6. The method of claim 5, wherein the additional therapeutic agent comprises an anti-cancer agent or an anti-inflammatory agent.

7. The method of claim 4, further comprising administering an effective amount of ionizing radiation to the subject.

8. A method of killing a tumor cell comprising contacting the tumor cell with an effective amount of a compound of claim 1, or a pharmaceutically acceptable salt thereof.

9. A pharmaceutical composition comprising a compound of claim 2, or a pharmaceutically acceptable salt thereof, and a pharmaceutically acceptable carrier.

10. A method of treating a cancer in a subject in need thereof comprising administering to the subject a therapeutically effective amount of a compound of claim 2, or a pharmaceutically acceptable salt thereof.

11. The method of claim 10, further comprising administering an additional therapeutic agent.

12. The method of claim 11, wherein the additional therapeutic agent comprises an anti-cancer agent or an anti-inflammatory agent.

13. The method of claim 10, further comprising administering an effective amount of ionizing radiation to the subject.

14. A method of killing a tumor cell comprising contacting the tumor cell with an effective amount of a compound of claim 2, or a pharmaceutically acceptable salt thereof.

* * * * *